(12) United States Patent
Lai

(10) Patent No.: US 10,117,778 B2
(45) Date of Patent: Nov. 6, 2018

(54) GOGGLE LENS

(71) Applicant: Wei-Xian Lai, Tainan (TW)

(72) Inventor: Wei-Xian Lai, Tainan (TW)

( * ) Notice: Subject to any disclaimer, the term of this patent is extended or adjusted under 35 U.S.C. 154(b) by 256 days.

(21) Appl. No.: 15/225,991

(22) Filed: Aug. 2, 2016

(65) Prior Publication Data

US 2017/0135860 A1 May 18, 2017

(30) Foreign Application Priority Data

Nov. 17, 2015 (TW) .............................. 104218416 U

(51) Int. Cl.
| | |
|---|---|
| *G02C 7/10* | (2006.01) |
| *A61F 9/02* | (2006.01) |
| *C09D 183/04* | (2006.01) |
| *G02B 1/10* | (2015.01) |
| *G02C 7/02* | (2006.01) |
| *G02B 5/28* | (2006.01) |

(52) U.S. Cl.
CPC ............ *A61F 9/022* (2013.01); *C09D 183/04* (2013.01); *G02B 5/283* (2013.01); *G02B 5/285* (2013.01); *G02C 7/10* (2013.01); *G02C 7/108* (2013.01); *G02B 1/10* (2013.01); *G02B 5/282* (2013.01); *G02C 7/022* (2013.01)

(58) Field of Classification Search
CPC ... A61F 9/028; A61F 9/04; A42B 3/20; A42B 3/2286; G02C 11/086; G02C 7/10
See application file for complete search history.

(56) References Cited

U.S. PATENT DOCUMENTS

| | | | | |
|---|---|---|---|---|
| 3,173,419 | A * | 3/1965 | Dubilier | .................. A61F 7/007 165/136 |
| 5,471,036 | A * | 11/1995 | Sperbeck | .................. H05B 3/36 2/435 |
| 9,678,367 | B2 * | 6/2017 | Cornelius | ............... G02C 11/08 |
| 2010/0226005 | A1 * | 9/2010 | Nishimoto | ............. G02B 1/115 359/359 |
| 2011/0274914 | A1 * | 11/2011 | Nakao | ................... A01G 9/1438 428/325 |

* cited by examiner

*Primary Examiner* — Tejash Patel
(74) *Attorney, Agent, or Firm* — Rosenberg, Klein & Lee

(57) ABSTRACT

A goggle lens is revealed. The goggle lens includes a first surface, a second surface opposite to the first surface, and a protective film connected to either the first surface or the second surface. The protective layer is a multi-layer structure formed by a silica composite film layer, a first zirconium dioxide film layer, a first silica film layer, an indium tin oxide (ITO) film layer, a second zirconium dioxide film layer and a second silica film layer in turn. Thereby harmful light such as blue light, infrared light, etc. is blocked by the protective film and ultraviolet light is also absorbed by the protective film for protecting user's eyes from damages.

8 Claims, 4 Drawing Sheets

GOGGLE LENS

BACKGROUND OF THE INVENTION

Field of the Invention

The present invention relates to a goggle lens, especially to a goggle lens with a multi-layer protective film that offers complete protection against harmful light such as blue light, infrared light, ultraviolet light etc.

Descriptions of Related Art

According to research papers, ultraviolet light and infrared light lead to continuous and cumulative damages to our eyes. Exposure to UV radiation has been implicated in serious eye disorders including cataract, aging of the eyes while infrared light results in cataract, retinal burns and corneal burns. In recent years, it is found that an overdose of UV light also causes macular degeneration.

The eyes are the windows of the soul. Thus the importance of the eyes is learned. In early days, wearing UV protective products is considered as an action to be a beauty. It seems only the female need to use these products. But now more research confirms that an overdose of UV light hurts our tissues and organs, especially our fragile eyes. Thus it is important to protect our eyes from damages caused by harmful light.

There is room for improvement and a need to provide a novel goggle lens.

SUMMARY OF THE INVENTION

Therefore it is a primary object of the present invention to provide a goggle lens that prevents harmful light from reaching users' eyes by a multi-layer film covered on surface thereof.

In order to achieve the above object, a goggle lens according to the present invention includes a lens body and a protective film. The lens body consists of a first surface and a second surface opposite to the first surface. The protective film is connected to either the first surface or the second surface. The protective layer is a multi-layer structure composed of a silica composite film layer, a first zirconium dioxide film layer, a first silica film layer, an indium tin oxide (ITO) film layer, a second zirconium dioxide film layer and a second silica film layer in turn. The protective film is connected to either the first surface or the second surface by the silica composite film layer.

The silica composite film layer is produced by a mixture of silicon monoxide and silicon dioxide.

The second zirconium dioxide film layer can be replaced by titanium pentoxide (Ti3O5).

The protective film further includes at least one second zirconium dioxide film layer and at least one second silica film layer arranged over the original second silica film layer in turn. The number of layers in the protective film is increased.

The goggle lens of the present invention has the following advantage. The goggle lens not only blocks blue light and infrared light but also absorbs harmful light such as ultraviolet light through the multi-layer structure of the protective film thereof. Thus the goggle lens protects eyes from damages caused by harmful light.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
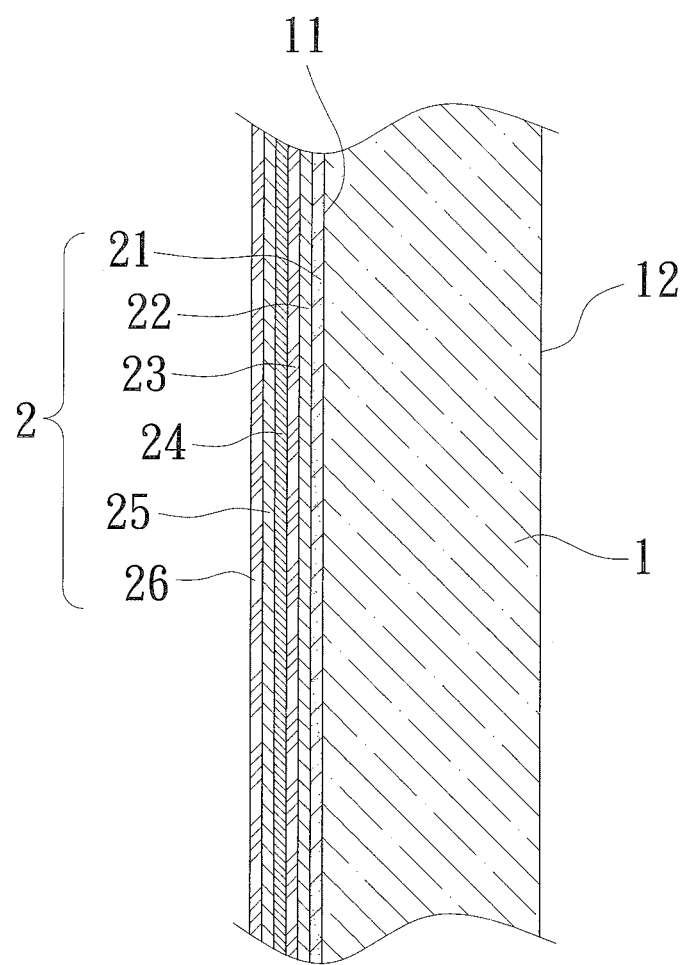
FIG. 1 is a partial enlarged view of an embodiment according to the present invention.

A goggle lens of the present invention mainly includes a lens body 1 and a protective film 2. The lens body 1 can be a flat lens, or an optical lens that corrects near-sighted or far-sighted. The lens body 1 consists of a first surface 11 and a second surface 12 opposite to the first surface 11.

The protective film 2 is connected to either the first surface 11 or the second surface 12 of the lens body 1. The protective film 2 is a multi-layer structure formed by a silica composite film layer 21, a first zirconium dioxide film layer 22, a first silica film layer 23, an indium tin oxide (ITO) film layer 24, a second zirconium dioxide film layer 25 and a second silica film layer 26 stacked in turn. The protective film 2 is connected to the first surface 11 by the silica composite film layer 21. The silica composite film layer 21 is produced by a mixture of silicon monoxide and silicon dioxide.

Figure 2:
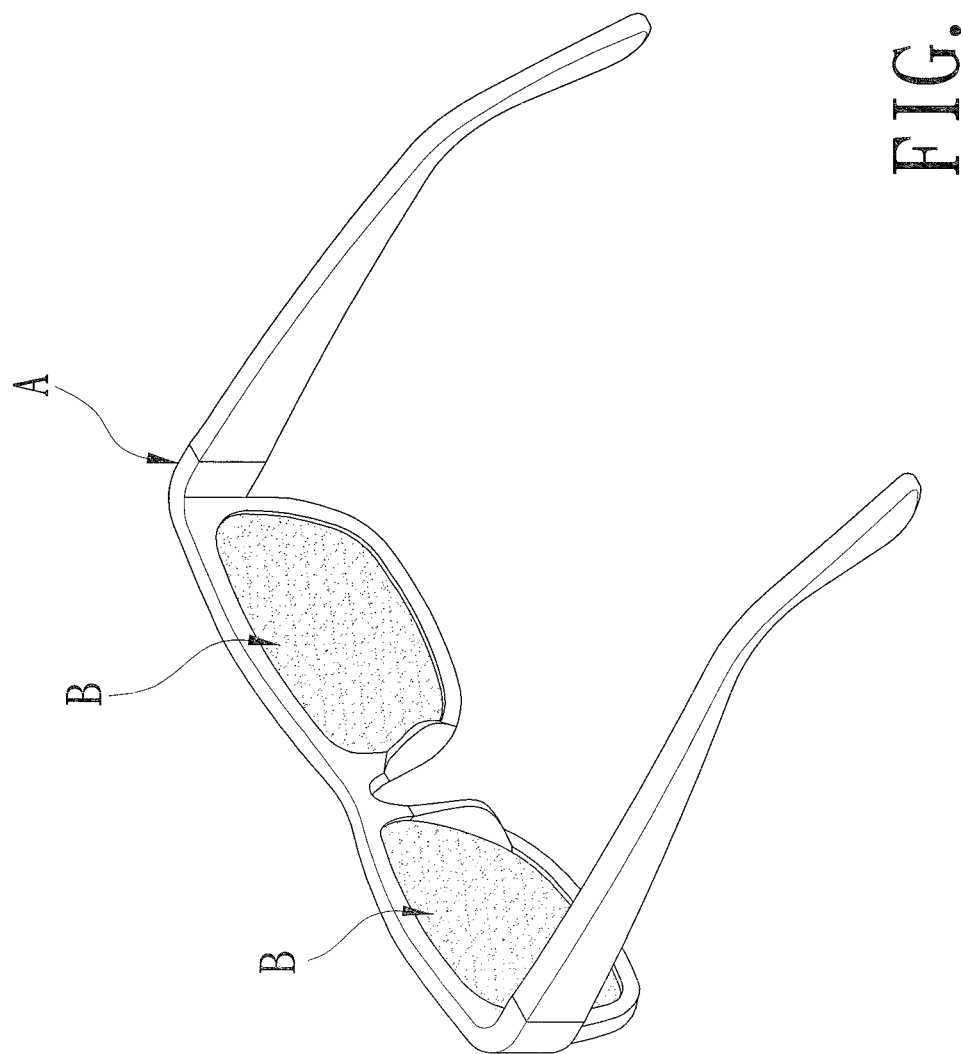
FIG. 2 is a schematic drawing showing an embodiment assembled on a pair of glasses according to the present invention.

Refer to FIG. 2, the lens B of the present invention not only blocks blue light and infrared light but also absorbs harmful light such as ultraviolet light through the multi-layer protective film 2 disposed on the first surface 11 of the lens body 1. When users wear glasses A disposed with the lenses B of the present invention, the lenses B of the present invention protect users' eyes from damages resulted from harmful light such as blue light, infrared light, ultraviolet light, etc.

Figure 3:
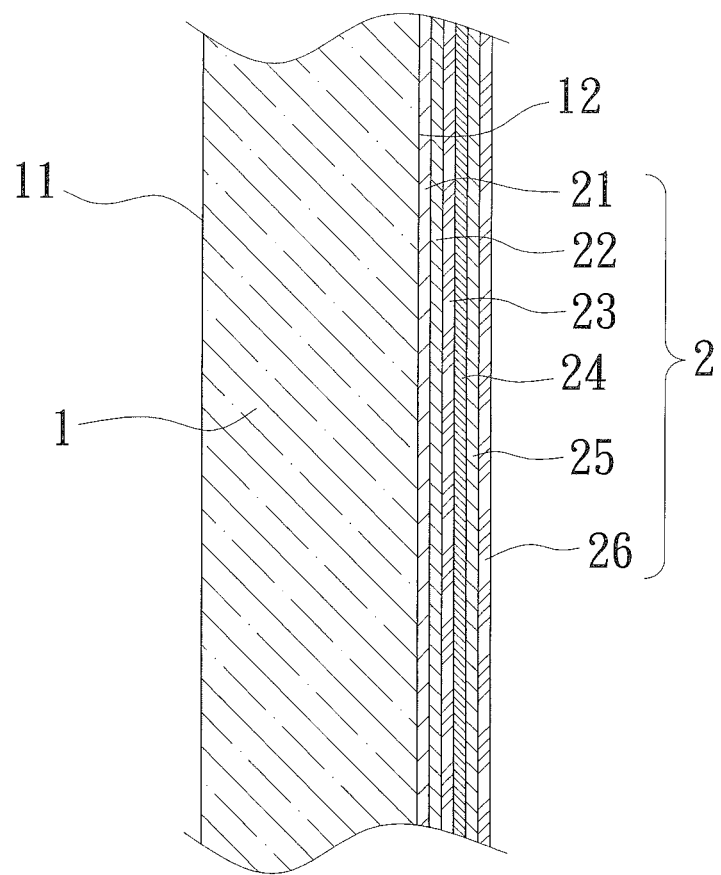
FIG. 3 is a partial enlarged view of another embodiment according to the present invention.

Refer to FIG. 3, another embodiment is revealed. In this embodiment, the protective film 2 is connected to the second surface 12 of the lens body 1 by the silica composite film layer 21.

Figure 4:
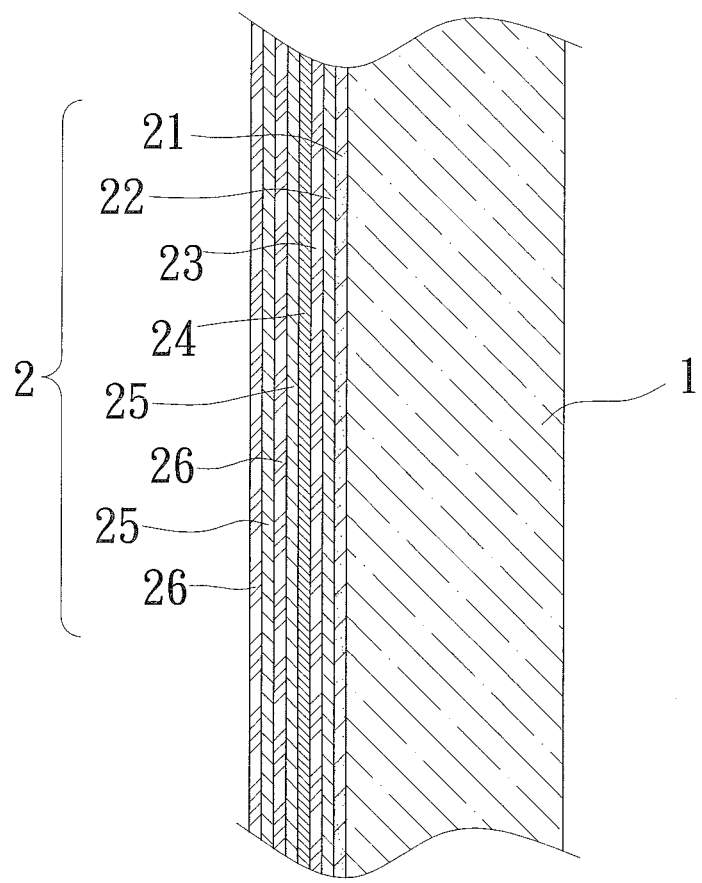
FIG. 4 is a partial enlarged view of a further embodiment according to the present invention.

Refer to FIG. 4, a further embodiment is revealed. In this embodiment, the protective film 2 further includes a second zirconium dioxide film layer 25 and a second silica film layer 26 arranged over the original second silica film layer 26 in turn. The number of layers in the protective film 2 is increased. Moreover, a combination of a second zirconium dioxide film layer 25 and a second silica film layer 26 can be arranged over the original second silica film layer 26 repetitively.

The second zirconium dioxide film layer 25 can be replaced by titanium pentoxide (Ti3O5) film (not shown in figure).

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A goggle lens comprising
a lens body and
a protective film;
wherein the lens body includes a first surface, and a second surface opposite to the first surface; and
wherein the protective film has multiple layers including a silica composite film layer, a first zirconium dioxide film layer, a first silica film layer, an indium tin oxide (ITO) film layer, a second zirconium dioxide film layer and a second silica film layer stacked in turn; the protective film is connected to either the first surface or the second surface by the silica composite film layer.

2. The device as claimed in claim 1, wherein the silica composite film layer is produced by a mixture of silicon monoxide and silicon dioxide.

3. The device as claimed in claim 2, wherein the second zirconium dioxide film layer is able to be replaced by titanium pentoxide (Ti3O5).

4. The device as claimed in claim 3, wherein the protective film further includes at least one second zirconium dioxide film layer and at least one second silica film layer arranged over the second silica film layer in turn; thus the number of layers in the protective film is increased.

5. The device as claimed in claim 1, wherein the second zirconium dioxide film layer is able to be replaced by titanium pentoxide (Ti3O5).

6. The device as claimed in claim 5, wherein the protective film further includes at least one second zirconium dioxide film layer and at least one second silica film layer arranged over the second silica film layer in turn; thus the number of layers in the protective film is increased.

7. The device as claimed in claim 2, wherein the protective film further includes at least one second zirconium dioxide film layer and at least one second silica film layer arranged over the second silica film layer in turn; thus the number of layers in the protective film is increased.

8. The device as claimed in claim 1, wherein the protective film further includes at least one second zirconium dioxide film layer and at least one second silica film layer arranged over the second silica film layer in turn; thus the number of layers in the protective film is increased.

* * * * *

UNITED STATES PATENT AND TRADEMARK OFFICE
CERTIFICATE OF CORRECTION

PATENT NO. : 10,117,778 B2  
APPLICATION NO. : 15/225991  
DATED : November 6, 2018  
INVENTOR(S) : Lai Page 1 of 1

It is certified that error appears in the above-identified patent and that said Letters Patent is hereby corrected as shown below:

On the Title Page

Item (12) should read:  
Yuan

Item (71) should read:  
Chi-Chou Yuan, Tainan (TW)

Item (72) should read:  
Chi-Chou Yuan, Tainan (TW)

Signed and Sealed this  
Seventeenth Day of December, 2019

Andrei Iancu  
*Director of the United States Patent and Trademark Office*